US010400579B2

(12) United States Patent
Vincelette et al.

(10) Patent No.: US 10,400,579 B2
(45) Date of Patent: Sep. 3, 2019

(54) OPTICAL DEVICE FOR MEASURING A PHYSICAL PARAMETER IN A HYDROGEN CONTAMINATED SENSING ZONE

(75) Inventors: André Vincelette, Deux-Montagnes (CA); Paul Lefebvre, Laval (CA); Jean-François Nadeu, Montreal (CA)

(73) Assignee: WEATHERFORD CANADA LTD., Edmonton Alberta (CA)

( * ) Notice: Subject to any disclaimer, the term of this patent is extended or adjusted under 35 U.S.C. 154(b) by 579 days.

(21) Appl. No.: 12/438,979

(22) PCT Filed: Aug. 31, 2007

(86) PCT No.: PCT/CA2007/001545
§ 371 (c)(1),
(2), (4) Date: Feb. 26, 2009

(87) PCT Pub. No.: WO2008/028277
PCT Pub. Date: Mar. 13, 2008

(65) Prior Publication Data
US 2009/0210168 A1    Aug. 20, 2009

Related U.S. Application Data

(60) Provisional application No. 60/825,019, filed on Sep. 8, 2006.

(51) Int. Cl.
E21B 47/06 (2012.01)
G01D 5/353 (2006.01)
G01N 21/77 (2006.01)

(52) U.S. Cl.
CPC ....... E21B 47/065 (2013.01); G01D 5/35303 (2013.01); G01N 21/774 (2013.01); E21B 47/06 (2013.01)

(58) Field of Classification Search
CPC .............................. E21B 47/06; E21B 47/065
(Continued)

(56) References Cited

U.S. PATENT DOCUMENTS 5,235,659 A    8/1993   Atkins et al.
5,287,427 A    2/1994   Atkins et al.
(Continued)

FOREIGN PATENT DOCUMENTS

EP         0 702 252       3/1996
WO     WO 2002/069003     9/2002
(Continued)

OTHER PUBLICATIONS

Becerra et al., "Nuclear Technology and Canadian Oil Sand," (2005).*
(Continued)

Primary Examiner — Hyun D Park

(57) ABSTRACT

A signal processing apparatus which has an input for receiving a signal conveying a response from first and second optical components to an optical excitation. The first and second optical components are in an optical sensor which is intended to be placed in a sensing zone. The sensing zone contains hydrogen susceptible to migrate into the optical sensor. The signal processing apparatus has a processing entity for processing the response from the first and second optical components to derive information on hydrogen concentration in the optical sensor.

33 Claims, 4 Drawing Sheets

(58) Field of Classification Search
USPC .......................................................... 702/23
See application file for complete search history.

(56) References Cited

U.S. PATENT DOCUMENTS

| | | | |
|---|---|---|---|
| 5,844,667 A * | 12/1998 | Maron | ........................ 356/35.5 |
| 6,146,713 A | 11/2000 | Cullen et al. | |
| 6,236,782 B1 | 5/2001 | Kewitsch et al. | |
| 6,237,406 B1 | 5/2001 | Nance | |
| 6,238,485 B1 | 5/2001 | Cullen et al. | |
| 6,238,729 B1 | 5/2001 | Cullen et al. | |
| 6,456,771 B1 | 9/2002 | Sanders | |
| 6,535,658 B1 * | 3/2003 | Mendoza | ........... G01N 21/7703 250/227.11 |
| 6,578,388 B1 | 6/2003 | Kewitsch et al. | |
| 6,702,897 B2 | 3/2004 | Cullen et al. | |
| 6,740,866 B1 * | 5/2004 | Bohnert et al. | .......... 250/227.14 |
| 7,068,897 B2 | 6/2006 | Russell et al. | |
| 7,126,680 B2 * | 10/2006 | Yamate et al. | ............... 356/73.1 |
| 2003/0194167 A1 * | 10/2003 | Wang et al. | .................... 385/12 |
| 2004/0067018 A1 | 4/2004 | Canning et al. | |
| 2004/0161215 A1 | 8/2004 | Wiley | |
| 2004/0165859 A1 | 8/2004 | Maklad et al. | |
| 2004/0173004 A1 | 9/2004 | Eblen, Jr. et al. | |
| 2004/0223694 A1 | 11/2004 | Dower et al. | |
| 2004/0234221 A1 | 11/2004 | Kringlebotn et al. | |
| 2005/0031981 A1 | 2/2005 | Sakamoto et al. | |
| 2005/0034873 A1 * | 2/2005 | Coon | .................... E21B 47/123 166/380 |
| 2005/0118064 A1 | 6/2005 | Berg | |
| 2005/0185189 A1 * | 8/2005 | Grossman | .......... G01K 11/3206 356/480 |
| 2007/0286561 A1 * | 12/2007 | Poland | ............... G02B 6/02042 385/126 |

FOREIGN PATENT DOCUMENTS

| | | |
|---|---|---|
| WO | WO 2002/100794 | 12/2002 |
| WO | WO 2004/095096 | 11/2004 |
| WO | WO 2006/021569 | 3/2006 |
| WO | WO 2008/028277 A1 | 3/2008 |

OTHER PUBLICATIONS

Trouillet et al., "Fibre grating for hydrogen sensing," Meas. Sci. Technol. (2006).*

Peng et al., "The characterization of hydrogen sensors based on palladium electroplated fiber Bragg gratings (FBG)," SPIE (1999).*

International Search Report issued in PCT/CA2007/001545.

Written Opinion of the International Searching Authority issued in PCT/CA2007/001545.

S. A. Vasiliev et al., "Increased solubility of molecular hydrogen in UV-exposed germanosilicate fibers", Jan. 1, 2006, vol. 31, No. 1, Optics Letters, p. 11-13.

P. L. Swart et al., "Study of hydrogen diffusion in boron/germanium codoped optical fibers", Journal of Lightwave Technology, vol. 20, No. 11, Nov. 2002, p. 1933-1941.

C. L. Liou et al., "Characteristics of hydrogenated fiber Bragg gratings", Appl. Phys. A (Materials Science & Processing), Appl. Phys., vol. A64, No. 2, Feb. 1997, p. 191-197.

R. Normann et al., "Development of fiber optic cables for permanent geothermal wellbore deployment", Proceedings, Twenty-Sixth Workshop on Geothermal Reservoir Engineering, Stanford University, Stanford, California, Jan. 29-31, 2001, SGP-TR-168, 9 pages.

J. L. Archambault, "3-Photosensitivity of germanosilicate optical fibres-3.5.3 Hydrogen-loading", Ph. D. Thesis, 1994, University of Southampton, p. 57-62.

C. Y. Wei et al., "The influence of hydrogen loading and the fabrication process on the mechanical strength of optical fibre Bragg gratings", Optical Materials 20 2002, p. 241-251.

* cited by examiner

OPTICAL DEVICE FOR MEASURING A PHYSICAL PARAMETER IN A HYDROGEN CONTAMINATED SENSING ZONE

CROSS-REFERENCE TO RELATED APPLICATION

The present application claims the benefit under 35 USC § 119(e) of prior U.S. provisional patent application Ser. No. 60/825,019 filed on Sep. 8, 2006, hereby incorporated by reference herein.

FIELD OF THE INVENTION

The invention relates to optical measuring devices and in particular to a measuring device, components thereof and methods for measurement for applications where the sensing zone in which the measurement is to be made contains hydrogen that can potentially contaminate optical components of the optical measuring device.

BACKGROUND OF THE INVENTION

The effects of hydrogen diffusion into optical fibers have been studied for more than a decade. Four principal aspects have been the objects of these studies: enhancing the photosensitivity of optical fibers, Bragg wavelength shift due to an increase of the effective index of optical fiber, absorption losses increase and hydrogen sensing.
More specifically, the presence of hydrogen molecules in the optical fiber changes its effective refractive index ($n_{ef}$). When a Bragg grating is present in the optical fiber, the resulting reflected Bragg wavelength ($\lambda_B$) as described by the Bragg condition equation is affected by the refractive index change:

$$\lambda_B = 2n_{eff}\Lambda \quad (1)$$

where $\Lambda$ is the period between the fringes of different refractive indexes.

Another effect of the presence of molecular hydrogen into an optical fiber is the increased attenuation of the light energy traveling through it, via molecular absorption. This phenomenon has an impact on fiber optics based monitoring systems for oil and gas extraction where pressure, temperature and environmental hydrogen concentration are usually quite high.

It is known to use either Bragg wavelength shift or absorption losses increase due to the presence of molecular hydrogen in the core of an optical fiber to monitor the concentration of hydrogen in the environment, or in other substances that would chemically react to create hydrogen. This type of sensors can have a very slow dynamic reactive time because it is limited by the diffusion rate of hydrogen through the glass of the optical fiber until it reaches the core of the fiber. Typically it takes a month to reach 97.3% of the equilibrium concentration of hydrogen for a standard 125 microns diameter fiber at 20° C. For that reason, most hydrogen sensors based on fiber Bragg gratings use a hydrogen-reactive coating, such as a palladium-based coating, that swells by absorbing hydrogen, and so, strain the fiber segment containing the Bragg grating increasing the refractive indexes fringes ($\Lambda$).

There is a need in the industry to provide optical measuring devices that can operate in sensing zones containing hydrogen, that are of simple construction, are reliable and provide accurate measurements results.

SUMMARY OF THE INVENTION

As embodied and broadly described herein the invention provides a signal processing apparatus which has an input for receiving a signal conveying a response from first and second optical components to an optical excitation. The first and second optical components are in an optical sensor which is intended to be placed in a sensing zone. The sensing zone contains hydrogen susceptible to migrate into the optical sensor. The signal processing apparatus has a processing entity for processing the response from the first and second optical components to derive information on hydrogen concentration in the optical sensor.

As embodied and described herein the invention also provides a measurement apparatus having an optical sensor for use in a sensing zone containing hydrogen susceptible to migrate into the optical sensor. The optical sensor has first and second optical components for generating a response to optical excitation impressed in the optical sensor. The measurement apparatus has an input for receiving the response generated by the first and second optical components and a processing entity for processing the response to derive information on hydrogen concentration in the optical sensor.

As embodied and described herein the invention also provides an apparatus for measuring a physical parameter. The apparatus has an optical sensor for exposure to the physical parameter, the optical sensor capable of producing a response dependent on the intensity of the physical parameter acting on the optical sensor. The optical sensor is susceptible to contamination by hydrogen potentially present in the vicinity of the optical sensor. The apparatus also has a processing entity in communication with the optical sensor for processing the response to derive a measure of the physical parameter intensity corrected for hydrogen contamination. The processing operation including determining from information contained in the response a degree of attenuation an optical signal manifests in the optical sensor, in at least at two different ranges of wavelengths of light.

As embodied and broadly described herein the invention also provides a method for measuring a physical parameter in a sensing zone, the method comprising placing an optical sensor in the sensing zone, the optical sensor including a plurality of optical components responsive to the intensity of the physical parameter acting on the optical sensor. The optical sensor is susceptible to contamination by hydrogen potentially present in the sensing zone which alters the response manifested by the optical components to the physical parameter. The method also includes introducing an optical excitation in the optical sensor and observing the response of the optical components to the optical excitation, the optical components responding to different ranges of wavelengths of light in the optical excitation. The method also includes processing the response of the optical components to derive a measure of the physical parameter intensity corrected for hydrogen contamination.

As embodied and broadly described herein, the invention also provides a method to derive information on hydrogen concentration in an optical sensor located in a sensing zone containing hydrogen susceptible to migrate into the optical sensor. The method includes receiving a signal conveying a response from first and second optical components of the optical sensor to an optical excitation and processing the response from the first and second optical components to derive information on hydrogen concentration in the optical sensor.

As embodied and broadly described herein, the invention also provides a method for measuring hydrogen concentration in an optical sensor. The method includes receiving a signal conveying a response from the optical sensor to an optical excitation and processing the response to derive a measure of the hydrogen concentration in the optical sensor. The processing operation includes determining from information contained in the response a degree of attenuation an optical signal manifests in the optical sensor, in at least at two different ranges of wavelengths of light.

As embodied and broadly described herein the invention also provides an apparatus for measuring temperature in a well of an oil extraction installation. The apparatus has an optical sensor for placement in the well which contains hydrogen susceptible to migrate into the optical sensor. The apparatus also has a signal processing device for processing an optical response of the optical sensor and derive from the optical response a temperature measurement in the well corrected for effects of hydrogen migration into the optical sensor.

As embodied and broadly described herein the invention also provides a method for measuring temperature in a well of an oil extraction installation, the method comprising the step of receiving an optical response from an optical sensor placed in the well which contains hydrogen susceptible to migrate into the optical sensor. The method also includes performing signal processing on information conveyed in the optical response and deriving from the information a temperature measurement in the well corrected for effects of hydrogen migration into the optical sensor.

As embodied and broadly described herein the invention further includes an optical sensor for measuring temperature in a well of an oil extraction installation, the well contains hydrogen susceptible to migrate into the optical sensor. The optical sensor has a first optical component and a second optical component and a common optical path containing the first optical component and the second optical component. The first and second optical components are capable of generating an optical response to an optical excitation conveying information from which can be derived a temperature measurement corrected for effects of hydrogen migration into the optical sensor.

BRIEF DESCRIPTION OF THE DRAWINGS

A detailed description of examples of implementation of the present invention is provided hereinbelow with reference to the following drawings, in which.

Figure 1:
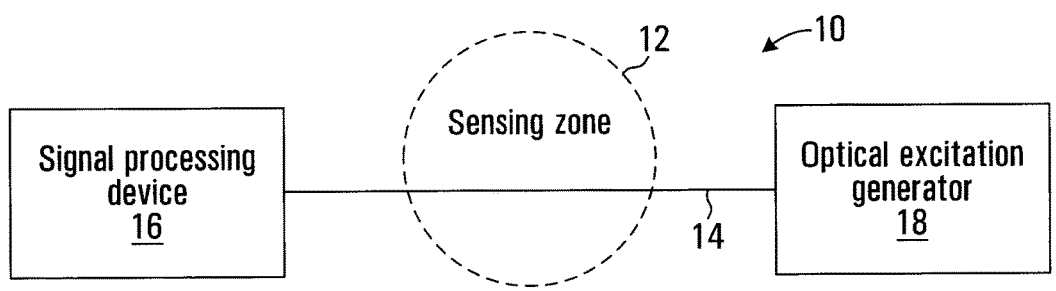
FIG. 1 is block diagram of a measuring apparatus according to a non-limiting example of implementation of the invention.

In the drawings, embodiments of the invention are illustrated by way of example. It is to be expressly understood that the description and drawings are only for purposes of illustration and as an aid to understanding, and are not intended to be a definition of the limits of the invention.

DETAILED DESCRIPTION

FIG. 1 shows a measurement apparatus 10 that measures the intensity of a physical parameter, such as temperature, pressure of strain. The measurement is performed in a sensing zone 12. Generally, the measurement apparatus 10 has an optical sensor 14 which is located in the sensing zone 12, a signal processing device 16 which performs an analysis of the optical response generated by the optical sensor 14, and an optical excitation generator 18 that injects into the optical sensor 14 an optical excitation.

The sensing zone 12 is the area where the measurement is to be made. In this specific example of implementation, the sensing zone 12 is susceptible to contain gaseous hydrogen. The hydrogen can migrate into the optical sensor and affect the way the sensor responds to the physical parameter. This will, in turn, produce an erroneous reading of the intensity of the physical parameter at the signal processing device 16 unless the measurement is corrected to take into account the hydrogen concentration. Specific applications where the measurement apparatus 10 can be used include oil and gas exploration/exploitation where the need exists for optical sensors that can reliably function in areas that often contain hydrogen gas.

Figure 2:
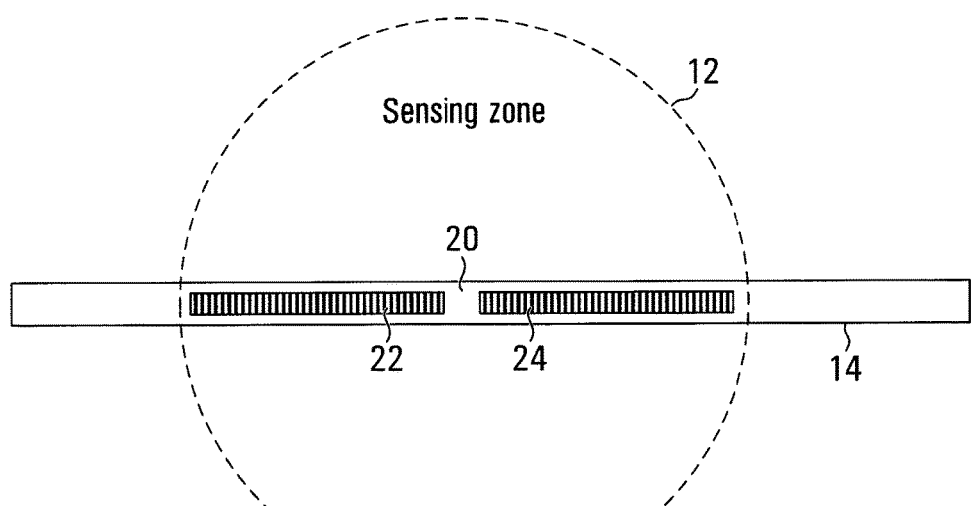
FIG. 2 is an enlarged view of the optical sensor of the apparatus shown in FIG. 1.

FIG. 2 shows in greater detail the optical sensor 14. The optical sensor 14 has a continuous length of optical fiber 20. The optical fiber 20 has a core. Hydrogen in the sensing zone 12 can migrate into the core of the optical fiber 20 which raises the index of refraction of the hydrogen containing section of the core. The optical sensor 14 has two optical components 22, 24 that respond to different ranges of wavelengths of light. In the example shown in the drawings, the optical components include gratings, such as straight Bragg gratings (the fringes are perpendicular to the optical fiber axis), a tilted Bragg grating or long period gratings. The optical components may also include Fabri-Perot or Mach-Zehnder type components. The optical components 22, 24 manifest in response to a change in intensity of the physical parameter acting on the optical components 22, 24, a shift in the range of wavelength filtered out from the optical excitation. For instance when the physical parameter is temperature, a rise or a drop in the temperature of the optical sensor 14 will cause the response of the optical components 22, 24 to change. This change is detected by the signal processing device 16 and used to obtain a measurement of the intensity of the physical parameter.

In use, the optical excitation generator 18 generates light which is injected into the optical fiber length that leads to the optical sensor 14. The optical excitation reaches the fiber gratings 22, 24 which filter out from the optical excitation two distinct wavelength ranges. Specifically, the wavelengths in the ranges of wavelengths of light to which the fiber gratings 22, 24 respond are reflected back toward the optical excitation generator such that the optical excitation that reaches the signal processing device 16 is lacking the wavelengths in those ranges. The signal processing device 16 uses the information it receives from the optical sensor 14 to derive the intensity of the physical parameter acting on the optical sensor 14 in the sensing zone 12, corrected for hydrogen concentration in the optical sensor. As indicated previously, the physical parameter can be the temperature, pressure or mechanical strain acting on the optical sensor 14. In the case of mechanical strain or pressure, there may be a necessity to mount the optical sensor 14 on a transducer structure (not shown in the drawings) that is directly exposed to pressure or mechanical strain and communicates this pressure or mechanical strain directly to the optical sensor 14. Such transducer structures are known in the art and do not need to be discussed here in greater details.

Note that while the specification discusses the fiber gratings 22, 24 as being responsive to respective ranges of wavelength, in practice those ranges are quite narrow, since in most practical applications the fiber gratings 22, 24 are designed to be as selective as possible. For the purposes of performing signal analysis on the fiber gratings 22, 24 responses, where a mathematical representation of a range of wavelengths may be overly complex, it is acceptable to represent the response of a fiber grating by a single wavelength, such as the peak wavelength in the range.

The signal processing device extracts from the response from the optical sensor 14 the wavelength ranges that have been filtered out by the gratings 22, 24 and also the degree at which the optical excitation has been attenuated in the optical sensor. The degree of optical excitation attenuation is due largely to the hydrogen concentration in the core of the optical sensor 14. These two elements of information can then be used to determine the hydrogen concentration in the core of the optical sensor 14, the temperature of the optical sensor 14, as well as the intensity of the physical parameter acting on the optical sensor 14 (other than temperature).

Techniques to determine the degree of attenuation of an optical signal in an optical fiber are generally known and will not be described in detail. Suffice it to say that a determination of the degree of attenuation can be made by comparing the amount of power received by the signal processing device 16 to the amount of power injected by the optical excitation generator 18. In instances where a direct measure of the amount of power injected by the optical excitation generator 18 is not readily available, a computation based on the nominal amount of power produced by the optical excitation generator can be used as a basis for calculating the degree of attenuation.

Figure 3:
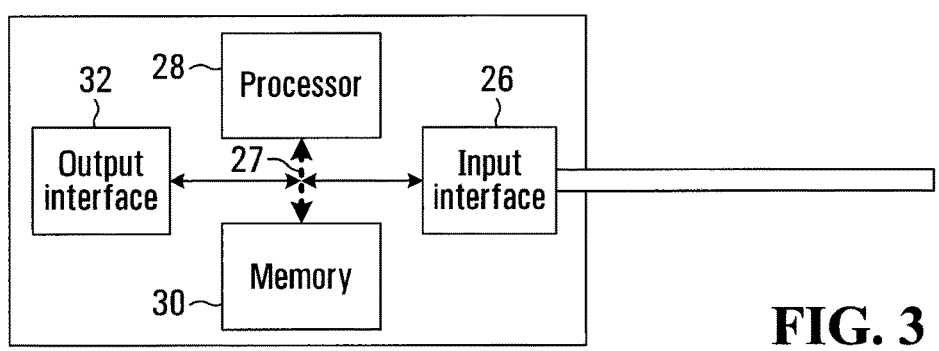
FIG. 3 is block diagram of the signal processing device of the measurement apparatus shown in FIG. 1.

FIG. 3 provides a block diagram of the signal processing device 16. The signal processing device 16 is based on a computer platform that enables to perform digital signal processing on the response received from the optical sensor 14 such as to derive the information desired. More specifically, the signal processing device 16 includes in input interface 26 that is coupled to the optical fiber length leading directly to the optical sensor 14. The input interface 26 will convert the signal into an electric digital signal, including performing appropriate filtering. The digital signal is then impressed on the data bus 27 that establishes a communication path between a processor 28 and a memory device 30. The processor 28 executes program code that defines a mathematical model establishing a relationship between the information that is available in the response received from the optical sensor 14 and the information that is sought, namely the hydrogen concentration, temperature and intensity of a physical parameter, other than temperature.

The signal processing device 16 also has an output interface 32 that allows communicating the result of the mathematical processing to an external entity. The external entity can be a human operator or a piece of equipment that uses the information generated by the signal processing device 16 for specific purposes.

Figure 7:
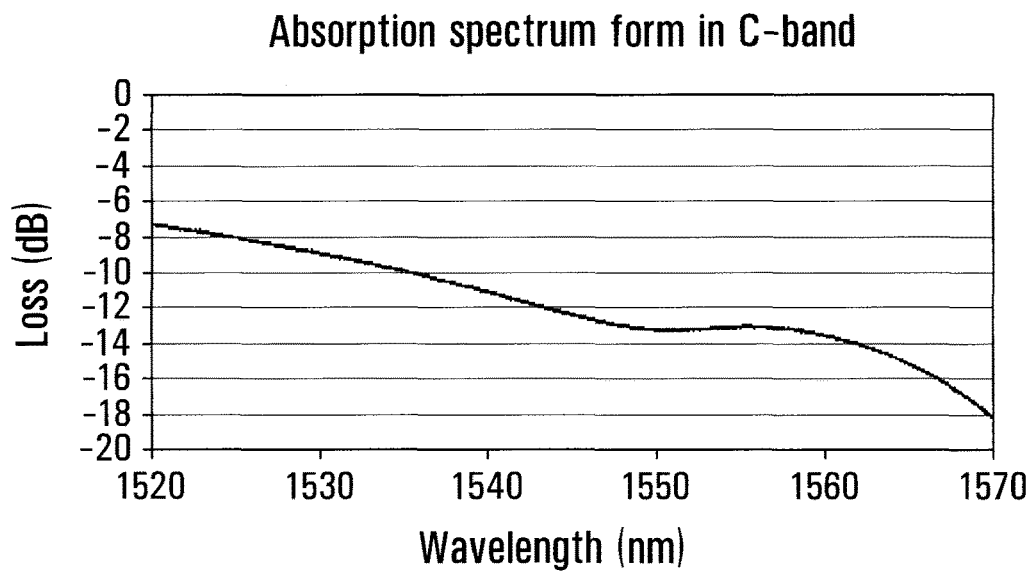
FIG. 7 is a graph illustrating the general profile of the hydrogen absorption spectrum in the telecommunication C-band window.
Figure 8:
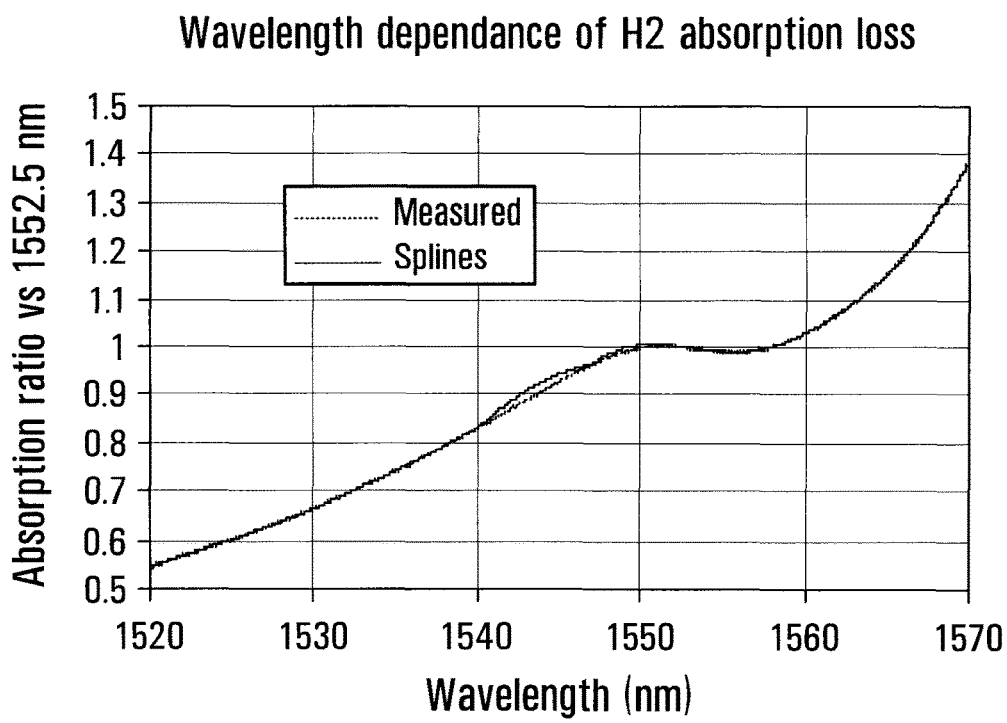
FIG. 8 is a graph showing the general profile of the hydrogen absorption spectrum in the telecommunication C-band window, normalized using the absorption at 1552.5 nm.

Molecular hydrogen absorbs photons according to their wavelength; FIG. 7 shows a typical hydrogen absorption spectrum over the C-band telecommunication window. The level of losses depends on the temperature (T), the molar concentration of hydrogen in the core ($[H_2]$) and the light path length (L), but the ratio of absorption is constant between two wavelengths. The absorption loss due the presence of hydrogen in the core of an optical fiber can be described by a relation of the following form:

$$H_2 \text{ loss } (\lambda, T) = A f(\lambda/\lambda_{ref}) g(T) [H_2] L \quad (2)$$

where $\lambda$ is the specific wavelength at which the absorption is calculated, g (T) is the increasing molecular absorption function with temperature of Arrhenius type, A is the absorption at the reference wavelength of one unitary concentration of hydrogen for one unity of length at the Arrhenius reference temperature and f ($\lambda/\lambda_{ref}$) is the function describing the ratio of absorption with wavelength normalized against a specific wavelength. Such a function, f ($\lambda/\lambda_{ref}$) is illustrated in FIG. 8, where absorption at 1552.5 nm is used as the normalization reference; in this case, the function has been represented using splines to approximate the relationship.

The presence of hydrogen in the optical sensor 14 also raises its effective index, shifting linearly the reflected Bragg wavelength:

$$\Delta\lambda_B = B[H2] \quad (3)$$

The temperature also raises effective index of the optical fiber, shifting independently and also linearly the reflected Bragg wavelength:

$$\Delta\lambda_B = B[H2] + C(T - T_{ref}) \quad (4)$$

By using two optical components 22, 24 in the form of fiber gratings at very close proximity to one another, one can assume that they are for all practical purposes at the same location, so the temperature, light path length and hydrogen concentration in the core of the optical sensor 14 are the same for both optical components 22, 24. The difference in absorption losses is then given by:

$$H_2 \text{ loss } (\lambda_1, T) - H_2 \text{ loss } (\lambda_2, T) = \{A\ g(T)\ [H_2]L\}\{f(\lambda_1/\lambda_{ref}) - f(\lambda_2/\lambda_{ref})\} \quad (5)$$

The signal processing device 16 can determine using known signal processing techniques the wavelength ranges to which the fiber gratings 22, 24 respond and the degree of attenuation the optical excitation has been subjected to by the optical sensor 14. This can therefore yield {$H_2$ loss ($\lambda_1$, T)–$H_2$ loss ($\lambda_2$, T)}, $\lambda_1$ and $\lambda_2$. The model characterization supplies all the other parameters except for the temperature and hydrogen concentration. Using equations (4) and (5), it is possible to solve the mathematical system using standard methods and obtain the values of hydrogen concentration and temperature in the core of the optical sensor 14 where the fiber gratings 22, 24 are located.

Figure 5:
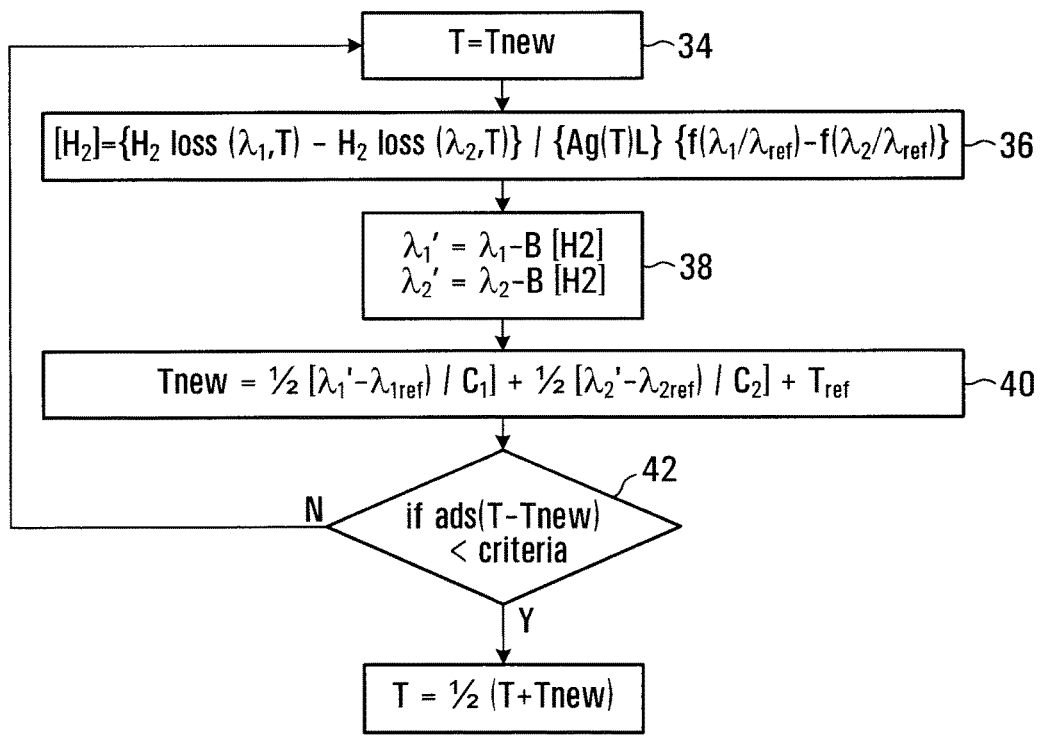
FIG. 5 is a flowchart of an iterative algorithm executed by the signal processing device shown in FIG. 3 to calculate the temperature and hydrogen concentration in the optical sensor using peak wavelength shift and the difference in absorbed light of two proximal fiber gratings at different wavelength ranges.

Several mathematical methods can be used to resolve these equations. FIG. 5 is an example of an iterative algorithm that is executed by the processor 28. The algorithm is a convergent iterative scheme that computes the hydrogen concentration and the temperature. The process begins at step 34 which assumes a temperature value. Step 36 uses then equation (5) to calculate the hydrogen concentration in the core of the optical sensor 14. Once the hydrogen concentration is known, the responses of the gratings 22, 24 are corrected for the hydrogen concentration effect, at step 38. Step 40 then computes anew the temperature from the remaining peak wavelength shifts. Step 42 compares the assumed temperature at step 34 to the calculated one; if the difference is too large (step 42), the algorithm is run one more time, the new iteration using the calculated temperature as the estimation. Since the mathematical system is naturally convergent, this process will result into a solution after a number of iterations. The solution provides both a temperature and hydrogen concentration values in the core of the optical sensor 14.

Note that since the mathematical system has two unknowns, the hydrogen concentration and the temperature, and three equations are available, equation (5) and one equation (4) for each fiber grating wavelength shift, the fiber gratings wavelength shifts can be used to measure another parameter or measurand (M) such as the intensity of the physical parameter acting on the optical sensor 14, other than temperature for which a result is already available. As indicated earlier, strain on the optical sensor causes an increase of the period of the fringes of refractive index ($\Lambda$), and so shifts the Bragg wavelength linearly according to equation (1) and independently of hydrogen or thermal effects. Using transducer structures as discussed above, several measurands, such as force, pressure, can be converted into strain of the fiber. Then:

$$\Delta\lambda_B = B[H2] + C(T-T_{ref}) + D(M-M_{ref}) \qquad (6)$$

Figure 6:
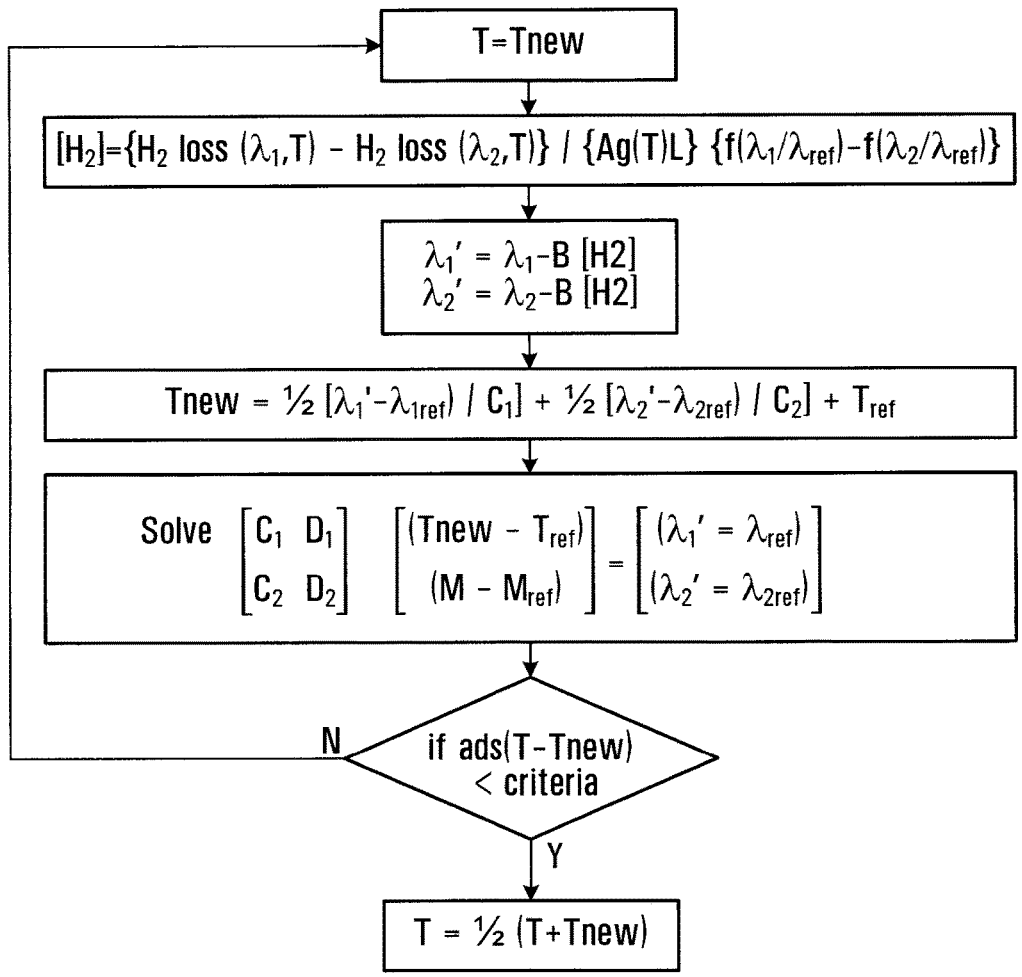
FIG. 6 is a flowchart of the iterative algorithm according to a variant.

FIG. 6 is a slightly modified iterative algorithm to enable the fiber gratings 22, 24 to measure a third independent measurand, such as the intensity of pressure or mechanical strain. The only difference with the previous algorithm is that the temperature calculation is changed by solving a two parameters matrix. It should be expressly noted that the algorithms discussed earlier are only examples of methods to obtain the information desired from the responses from the gratings 22, 24 and the invention should not be limited to those methods since other techniques can also be used without departing from the spirit of the invention.

Figure 4:
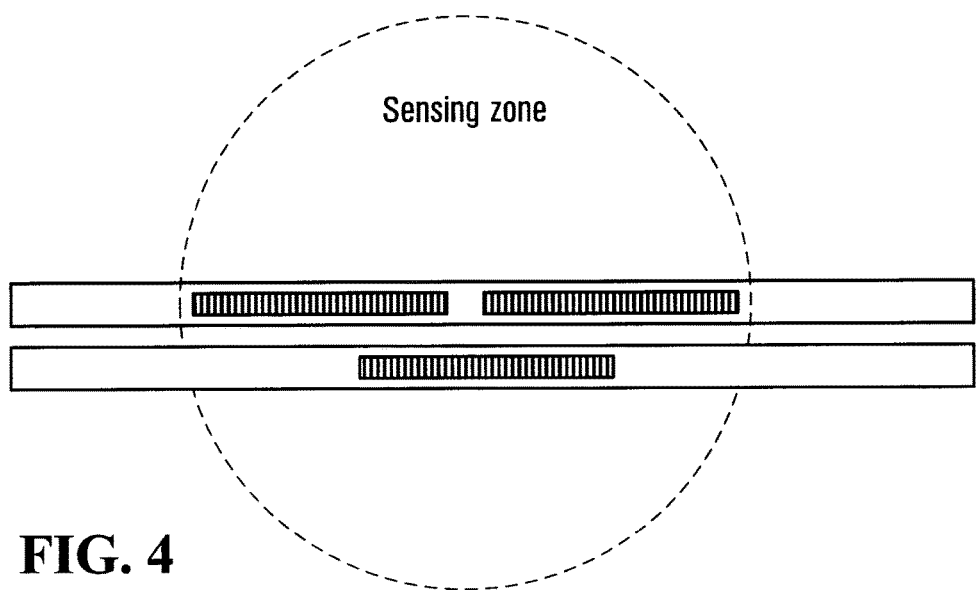
FIG. 4 is a diagram of a measuring apparatus according to a variant.

FIG. 4 shows a variant of the optical sensor discussed in FIG. 2. In this example, the optical sensor has two optical fibers, one fiber containing a pair of closely spaced Bragg gratings that are used primarily to compute the hydrogen concentration in the sensing zone. Another Bragg grating, located in a separate optical fiber that is adjacent the pair of gratings, is used to measure the intensity of the physical parameter acting on the optical sensor in the sensing zone. The response of the single Bragg grating can be corrected to compensate for the hydrogen concentration computed based on the response obtained from the pair of Bragg gratings.

The above examples of implementation of the invention have all been discussed in the context of systems using optical responses based on signal transmission through optical components. In other words, the information conveyed in the response is carried in the part of the optical excitation passing through the optical components. It is also possible to use systems based on signal reflection where the response resides in the portion of the optical excitation that is reflected instead of being transmitted.

The various embodiments discussed earlier can be used for different practical applications. One example is the field of oil/gas exploration where it is often required to obtain temperature measurements in deep wells that contain a sufficient concentration of hydrogen gas, which as discussed earlier can migrate into the optical sensor and affect its index of refraction.

Specifically, the extraction of oil from oil sands requires the injection of steam into a well that softens the bitumen sufficiently allowing it to flow to the surface via a collection conduit. For operational reasons, it is necessary to monitor the temperature inside the steam well with reasonable accuracy. Temperature measuring devices constructed according to the principles of the present invention have been found satisfactory. Specifically, since those devices are optical they do not require electrical energy to operate and, therefore, do not create a risk of explosion due to the high concentration of gases capable of igniting and burning. In addition, they measuring devices can correct the raw measurements for the effects of hydrogen diffusion and thus produce accurate results.

Although various embodiments have been illustrated, this was for the purpose of describing, but not limiting, the invention. Various modifications will become apparent to those skilled in the art and are within the scope of this invention, which is defined more particularly by the attached claims.

The invention claimed is:

1. A system for measuring a physical parameter, comprising:
   (a) an optical sensor for installation in a hydrogen-contaminated sensing zone, the optical sensor being configured to measure the physical parameter in the sensing zone, the optical sensor comprising:
      (i) an optical path; and
      (ii) first and second optical elements in the optical path, the first and second optical elements being spaced from each other along a direction of an optical excitation configured to propagate in the optical path by a distance that does not exceed in size the sensing zone, such that:
         (1) hydrogen ingression in the optical path affects the first and second optical elements in substantially the same way; and
         (2) the first and second optical elements remain at about the same temperature, wherein the first and second optical elements are configured for interacting with the optical excitation propagating in the optical path to generate an optical response also propagating in the optical path, the optical response including a first component which conveys a response of the first optical element to the optical excitation and a second component that conveys a response of the second optical element to the optical excitation, the hydrogen ingression in the optical path inducing an error in the measurement of the physical parameter conveyed by the optical response; and
   (b) a signal processing apparatus having an input coupled to the optical path receiving the optical response, the signal processing apparatus including a processor being configured to use an iterative process to derive, from the first and the second components, an adjusted measurement of the physical parameter in the sensing zone adjusted for the error using:
      (i) absorption loss due to the hydrogen ingression in the optical path; and
      (ii) a hydrogen concentration value in the sensing zone, wherein the iterative process updates the hydrogen concentration value and the adjusted measurement of the physical parameter.

2. The system as defined in claim 1, wherein at least a portion of the optical path is defined by a continuous length of optical fiber, the first optical element and the second optical element being located in the continuous length of the optical fiber.

3. The system as defined in claim 2, wherein the processor is configured to derive the adjusted measurement of the physical parameter adjusted for the error by using as a factor a degree of attenuation induced by the optical sensor on an optical signal propagating through the optical sensor.

4. The system as defined in claim 3, wherein the processor is configured to derive the adjusted measurement of the physical parameter adjusted for the error by using as a factor a degree of attenuation induced by the first optical element on the optical signal propagating through the optical sensor.

5. The system as defined in claim 4, wherein the first optical element is configured to reflect a first predetermined wavelength range from the optical excitation.

6. The system as defined in claim 5, wherein the processor is configured to derive the adjusted measurement of the physical parameter adjusted for the error by using as a factor a degree of attenuation induced by the first optical element in the first predetermined wavelength range.

7. The system as defined in claim 6, wherein the second optical element is configured to reflect a second predetermined wavelength range from the optical excitation.

8. The system as defined in claim 7, wherein the processor is configured to derive the adjusted measurement of the physical parameter adjusted for the error by using as a factor a degree of attenuation induced by the second optical element in the second predetermined wavelength range.

9. The system as defined in claim 8, wherein the first predetermined wavelength range is different from the second predetermined wavelength range.

10. The system as defined in claim 1, wherein the physical parameter is temperature.

11. The system as defined in claim 1, wherein the physical parameter is strain.

12. The system as defined in claim 1, wherein the physical parameter is pressure.

13. A method for measuring a physical parameter in a hydrogen-contaminated sensing zone, the method comprising:
(a) introducing an optical excitation into an optical sensor to generate an optical response, wherein the optical sensor is in the sensing zone, the optical sensor comprising:
(i) first and second optical elements responsive to an intensity of the physical parameter acting on the optical sensor; and
(ii) an optical path susceptible to hydrogen contamination as a result of migration of hydrogen present in the sensing zone into the optical path, wherein:
(1) the first and second optical elements are spaced from each other along a direction of the optical excitation propagating in the optical path by a distance that does not exceed in size the sensing zone;
(2) the optical response is generated when the optical excitation interacts with the first and second optical elements, the optical response conveying an intensity measurement of the physical parameter and including a first component which conveys a response of the first discrete optical element to the optical excitation and a second component that conveys a response of the second discrete optical element to the optical excitation; and
(3) hydrogen ingression in the optical path is configured to induce an error in the measurement of the physical parameter conveyed by the optical response; and
(b) processing the optical response by deriving from the optical response an adjusted measurement of the physical parameter adjusted for the error, wherein the deriving comprises using an iterative process to derive from the first and the second components the adjusted measurement of the physical parameter in the sensing zone adjusted for the error using:
(i) absorption loss due to the hydrogen ingression in the optical path; and
(ii) a hydrogen concentration value in the sensing zone, wherein the iterative process updates the hydrogen concentration value and the adjusted measurement of the physical parameter.

14. The method for measuring a physical parameter as defined in claim 13, wherein both the first and the second optical elements are exposed to substantially the same degree of hydrogen contamination.

15. The method for measuring a physical parameter as defined in claim 13, wherein both the first and the second optical elements are exposed to substantially the same temperature in the sensing zone.

16. The method for measuring a physical parameter as defined in claim 13, wherein the first and second optical elements include gratings.

17. The method as defined in claim 16, wherein deriving the adjusted measurement of the physical parameter adjusted for the error comprises using as a factor a degree of attenuation induced by the first optical element and a degree of attenuation induced by the second optical element, on an optical signal propagating through the optical sensor.

18. The method as defined in claim 13, wherein the physical parameter is temperature.

19. The method as defined in claim 13, wherein the physical parameter is strain.

20. The method as defined in claim 13, wherein the physical parameter is pressure.

21. The method of claim 13, further comprising operating a well according to the adjusted measurement of the physical parameter, the well containing the hydrogen-contaminated sensing zone.

22. A non-transitory computer-readable medium for measuring a physical parameter in a hydrogen-contaminated sensing zone, the computer-readable medium having instructions stored thereon which, when executed by one or more processors, perform operations comprising:
(a) introducing an optical excitation into an optical sensor to generate an optical response, wherein the optical sensor is in the sensing zone, the optical sensor comprising:
(i) first and second optical elements responsive to an intensity of the physical parameter acting on the optical sensor; and
(ii) an optical path susceptible to hydrogen contamination as a result of migration of hydrogen present in the sensing zone into the optical path, wherein:
(1) the first and second optical elements are spaced from each other along a direction of the optical excitation propagating in the optical path by a distance that does not exceed in size the sensing zone;
(2) the optical response is generated when the optical excitation interacts with the first and second optical elements, the response conveying an intensity of the physical parameter and including a first component which conveys a response of the first optical element to the optical excitation and a second component that conveys a response of the second optical element to the optical excitation; and (3) hydrogen ingression in the optical path is configured to induce an error in the intensity of the physical parameter conveyed by the optical response; and (b) processing the optical response by deriving from the optical response an adjusted measurement of the physical parameter adjusted for the error, wherein the deriving comprises using an iterative process to derive from the first and the second components the adjusted measurement of the physical parameter in the sensing zone adjusted for the error using:

(i) absorption loss due to the hydrogen ingression in the optical path; and (ii) a hydrogen concentration value in the sensing zone, wherein the iterative process updates the hydrogen concentration value and the adjusted measurement of the physical parameter.

23. The non-transitory computer-readable medium as defined in claim 22, wherein at least a portion of the optical path is defined by a continuous length of optical fiber, the first optical element and the second optical element being located in the continuous length of the optical fiber.

24. The non-transitory computer-readable medium as defined in claim 23, wherein deriving the adjusted measurement of the physical parameter adjusted for the error comprises using as a factor a degree of attenuation induced by the optical sensor on an optical signal propagating through the optical sensor.

25. The non-transitory computer-readable medium as defined in claim 24, wherein deriving the adjusted measurement of the physical parameter adjusted for the error comprises using as a factor a degree of attenuation induced by the first optical element on the optical signal propagating through the optical sensor.

26. The non-transitory computer-readable medium as defined in claim 25, wherein the first optical element is configured to reflect a first predetermined wavelength range from the optical excitation.

27. The non-transitory computer-readable medium as defined in claim 26, wherein deriving the adjusted measurement of the physical parameter adjusted for the error comprises using as a factor a degree of attenuation induced by the first optical element in the first predetermined wavelength range.

28. The non-transitory computer-readable medium as defined in claim 27, wherein the second optical element is configured to reflect a second predetermined wavelength range from the optical excitation.

29. The non-transitory computer-readable medium as defined in claim 28, wherein deriving the adjusted measurement of the physical parameter adjusted for the error comprises using as a factor a degree of attenuation induced by the second optical element in the second predetermined wavelength range.

30. The non-transitory computer-readable medium as defined in claim 29, wherein the first predetermined wavelength range is different from the second predetermined wavelength range.

31. The non-transitory computer-readable medium as defined in claim 22, wherein the physical parameter is temperature.

32. The non-transitory computer-readable medium as defined in claim 22, wherein the physical parameter is strain.

33. The non-transitory computer-readable medium as defined in claim 22, wherein the physical parameter is pressure.

* * * * *